United States Patent
Gord et al.

[19]

[11] Patent Number: 5,919,710
[45] Date of Patent: Jul. 6, 1999

[54] OPTICAL METHOD FOR QUANTITATING DISSOLVED OXYGEN IN FUEL

[75] Inventors: James R. Gord, Beavercreek, Ohio; Steven W. Buckner, Columbus, Ga.; William L. Weaver; Keith D. Grinstead, Jr., both of Beavercreek, Ohio

[73] Assignee: The United States of America as represented by the Secretary of the Air Force, Washington, D.C.

[21] Appl. No.: 08/920,350

[22] Filed: Jul. 16, 1997

Related U.S. Application Data

[60] Provisional application No. 60/022,226, Jul. 18, 1996.
[51] Int. Cl.$^6$ ................................................. G01N 21/64
[52] U.S. Cl. .................. 436/127; 436/27; 436/28; 436/29; 436/30; 436/56; 436/136; 436/138; 436/140; 422/82.05; 422/82.08; 250/458.1; 250/459.1; 250/461.1; 356/317; 356/318; 356/417
[58] Field of Search ................... 436/27, 28, 29, 436/30, 127, 136, 138, 56, 140, 172; 422/82.05, 82.08; 250/458.1, 459.1, 461.1; 356/317, 318, 417

[56] References Cited

U.S. PATENT DOCUMENTS

| | | | |
|---|---|---|---|
| 3,612,866 | 10/1971 | Stevens | 250/71 |
| 4,580,059 | 4/1986 | Wolfbeis et al. | 250/459.1 |
| 4,775,514 | 10/1988 | Barnikol et al. | 422/68 |
| 4,810,655 | 3/1989 | Khalil et al. | 436/138 |
| 5,043,285 | 8/1991 | Surgi | 436/136 |
| 5,108,932 | 4/1992 | Wolfbeis | 436/124 |

FOREIGN PATENT DOCUMENTS

| | | |
|---|---|---|
| 568558 | 10/1975 | Switzerland . |
| 9212424 | 7/1992 | WIPO . |

OTHER PUBLICATIONS

Draxler et al "Time–resolved floorescence spectroscopy for chemical sensors", Appl. Opt. (1996), 35(21), 4117–4123 Abstract only.

Viiimpoc et al. "Simultaneous measurement of particle size, mass rate of deposition, & oxygen concentration in thermally stressed jet fuel".

HTD CAm. Soc. Mech. Eng.) (1995, 321 (Proceedings of the ASME Heat Transfer and Fluids Engineering Divisions, 1995) pp. 343–350. Abstract only.

"Dissolved Oxygen Quantitation in Fuel Through Measurements of Dynamically Quenched Fluorescence Lifetimes," by Gord et al, IEEE Publication 95CH3482–7, pp. 39.1–39.6 (Jul. 1995).

*Primary Examiner*—Jeffrey Snay
*Assistant Examiner*—S. Carrillo
*Attorney, Agent, or Firm*—Bobby D. Scearce; Thomas L. Kundert

[57] ABSTRACT

A method for the quantitative determination of dissolved oxygen in a liquid fuel includes the steps of doping a sample of the fuel with a preselected concentration of a probe material including a luminophor which exhibits luminescence of wavelength which is quenched by oxygen dissolved in the fuel, illuminating the fuel with light from a coherent light source, such as a laser, of a wavelength which induces the luminescence in the luminophor, and thereafter measuring the change with time of the luminescence from the luminophor in the fuel and determing from the change with time of the luminescence the concentration of oxygen in the fuel.

6 Claims, 4 Drawing Sheets

OPTICAL METHOD FOR QUANTITATING DISSOLVED OXYGEN IN FUEL

This application claims the benefit of Provisional Application Ser. No. 60/022,226 filed Jul. 18, 1996.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for the quantitative determination of oxygen in liquid fuels, and more particularly to system and method for quantitation of dissolved molecular oxygen ($O_2$) in fuel by observing the quenching by dissolved oxygen of the fluorescence of a laser excited probe molecule in the fuel.

Prior art methods for determining dissolved oxygen concentration in liquid fuel are cumbersome and time-consuming as to be rendered substantially useless for many measurements. For example, methods based on gas chromatography (GC) and combined GC and mass spectrometry (MS) are sensitive to at least a few parts per million (ppm) $O_2$ and give results with fairly high precision. However, in the GC based method, the oxygen must be separated from the fuel prior to introduction to the GC column and, because any fuel in the GC sample degrades column efficiency, the column must be run through a heating cycle regularly to remove small amountsof fuel; GC is relatively slow and does not allow study of rapidly time-varying signals and is performed off-line which prevents in-situ and spatially resolved sample measurements; and GC based methods, and GC/MS based methods in particular, are relatively expensive to perform.

Electrochemical methods, such as potentiometry and voltammetry, can be used for analysis of oxygen. Oxygen is a reducible species detectable with high sensitivity by polarography in aviation fuel because of a paucity of other reducible species in the fuel; this method is relatively inexpensive and requires no separation of the oxygen from the fuel prior to measurement, but the interface between the fuel and the electrochemical cell is cumbersome and the measurement is slow, which substantially prevents use of the method for rapidly time-varying signals, and cannot be performed non-invasively. Oxygen is difficult to measure spectroscopically in organic solutions because $O_2$ does not absorb in the infrared and has electronic transitions in the far ultraviolet where organic solutions absorb strongly. Although $O_2$ has a Raman allowed transition and unique electron spin resonance, methods based on these attributes have low sensitivity, high cost and experimental complexity.

The invention solves or substantially reduces in critical importance problems with prior art methods as just described by providing an optical method for determining dissolved oxygen in fuel using the oxygen concentration dependence of the luminescence lifetime of an appropriate probe molecule doped in the fuel. The method of the invention is rapid, in that a single measurement can be made on a microsecond timescale and a signal comprising the average of 30 decays may be made in one second. The method is highly sensitive, non-intrusive, non-destructive, insensitive to thermal stressing of the fuel, less expensive than existing methods, and may be designed to obtain spatially-resolved profiling of oxygen concentration in fuel lines.

It is therefore a principal object of the invention to provide a method for determining dissolved oxygen in liquid fuel.

It is a further object of the invention to provide an optical method for the quantitative determination of dissolved oxygen in liquid fuel.

It is yet another object of the invention to provide a non-invasive method for determination of dissolved oxygen in liquid fuel.

It is a further object of the invention to provide a highly sensitive method for quantitatively determining the concentration of dissolved oxygen in liquid fuel by observing the laser excited fluorescence of a probe molecule in the fuel.

These and other objects of the invention will become apparent as a detailed description of representative embodiments proceeds.

SUMMARY OF THE INVENTION

In accordance with the foregoing principles and objects of the invention, a method for the quantitative determination of dissolved oxygen in a liquid fuel is described which in a preferred embodiment comprises the steps of doping a sample of the fuel with a preselected concentration of a probe material including a luminophor which exhibits luminescence of wavelength which is quenched by oxygen dissolved in the fuel, illuminating the fuel with light from a coherent light source, such as a laser, of a wavelength which induces the luminescence in the luminophor, and thereafter measuring the change with time of the luminescence from the luminophor in the fuel and determining from the change with time of the luminescence the concentration of oxygen in the fuel.

DESCRIPTION OF THE DRAWINGS

The invention will be more clearly understood from the following detailed description of representative embodiments thereof read on conjunction with the accompanying drawings wherein.

DETAILED DESCRIPTION

Figure 1:
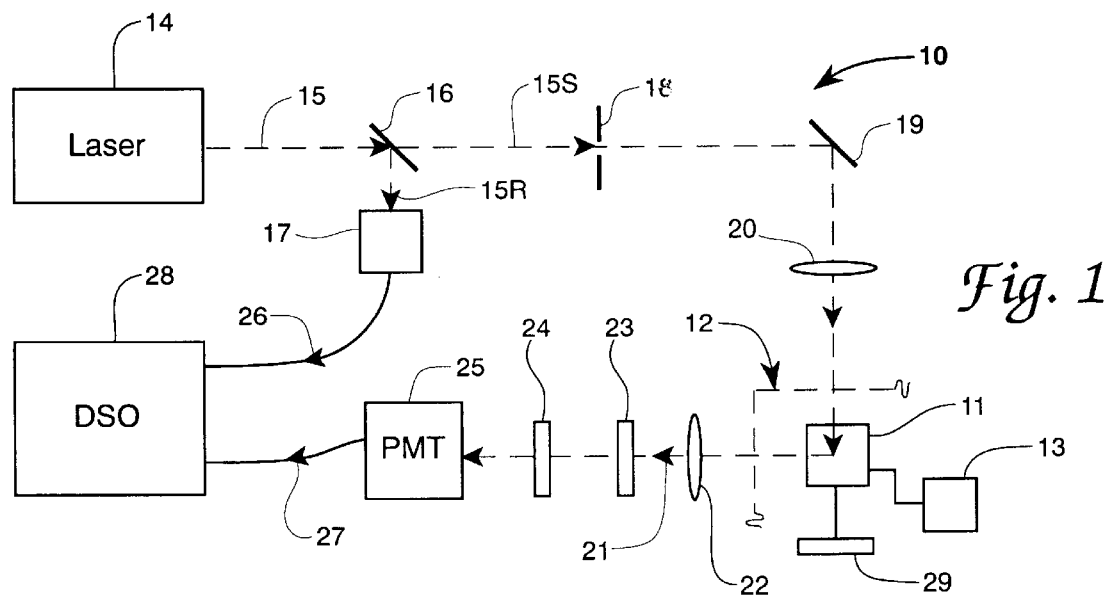
FIG. 1 is a schematic block diagram of a representative system useful in the practice of the method of the invention.

Theoretical considerations and experimental procedures for the quantitative determination of dissolved oxygen in liquid fuels according to the invention are described in Gord et al, "Dissolved Oxygen Quantitation in Fuel Through Measurements of Dynamically Quenched Fluorescence Lifetimes," IEEE Publication 95CH3482-7, pp 39.1–39.6 (Jul. 1995), the entire teachings of which are incorporated by reference herein.

In accordance with a governing principle of the invention, the oxygen molecule ($O_2$) efficiently quenches the luminescence of a variety of luminophors in fuels as a result of an energy match between the single-triplet gap in $O_2$ and the energies of the first excited state of many polycyclic aromatic hydrocarbons and of many metal complexes. Luminophors of interest in the practice of the invention exhibiting luminescence which is quenched by $O_2$ include pyrene, anthracene and napthalene and the derivatives thereof, or others as would occur to the skilled artisan practicing the invention. Variations in oxygen concentration will result in variations in the collision rate between oxygen and a luminophor (probe) present in a solution. Both the quantum yield and lifetime of the luminescence of the probe exhibit an inverse oxygen concentration dependence.

The principle of the invention may be illustrated by considering the photoexcitation of probe molecule A, the excited state A* which decays by luminescence with rate constant $k_L$ or is quenched by $O_2$ with a rate constant $k_q(Q)$:

$$A + photon \rightarrow A^* \rightarrow (k_f) \rightarrow A + photon \rightarrow k_q(Q) \rightarrow A + Q^* \quad (1)$$

The overall first order rate constant $k_s$ for Eq (1) is given by:

$$k_s = k_L + k_q(Q) \quad (2)$$

The integrated rate expression for the decay of the excited states of A is:

$$A_t = A_0 \exp(-k_s t) \quad (3)$$

A single excited state will show a simple exponential decay. Eq (2) shows that determination of the rate constant for the decay of the excited state at a series of oxygen concentrations yields a straight line. For the best operating mode in the invention the lifetime $\tau$ for the decay of the excited state equals $1/k$. Eq (2) can be expressed using the lifetime of the unquenched excited state $\tau_0$ and the lifetime of the excited state at a concentration Q of quencher $\tau_q$ as:

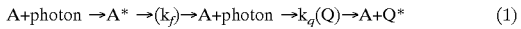

$$Q\, \tau_0/\tau_q + 1 = \tau_0/\tau_s \quad (4)$$

where $$1/\tau_s = k_s \quad (5)$$

Eq (4) is the Stern-Volmer equation (see Lakowica, *Principles of Fluorescence Spectroscopy*, Plenum Press, NY (1983), incorporated by reference herein), and can be used as a calibration equation with $\tau_0/\tau_s$ plotted versus $O_2$ concentration.

Referring now to the drawings, FIG. 1 is a schematic block diagram of representative system 10 useful in the determination of $O_2$ concentration in a liquid fuel according to the method of the invention. In system 10, a liquid fuel sample 11 to be tested is disposed within a sample region 12, which may include a cuvette, flask, cell, flowing fuel line, or other suitable disposition occurring to the skilled artisan practicing the invention. Sample 11 comprises a liquid fuel such as cyclohexane, isooctane, Jet-A, hexane, heptane, nonane, decane, kerosene, oil or other fuel the oxygen content of which is sought. Sample 11 is doped with a known concentration of a probe 13 molecule selected from the class of luminophors known in the art as suitable for the intended purpose, including those listed above. A coherent light source such as laser source 14 provides light beam 15 for exciting probe 13 in sample 11. Sources 14 suitable for use in the method of the invention include pulsed nitrogen, Eximer, Nd:YAG, Nd:YLF, Ti:sapphire, and Nd:YVO$_4$ lasers, or other source as would occur to the skilled artisan practicing the invention. Beam 15 is split by beamsplitter 16 into reference beam portion 15R directed onto detector 17 (such as a photodiode, photomultiplier, external trigger or other equivalent purpose detector) and sample beam portion 15S directed onto sample 11. Beam 15S may be directed onto sample 11 through any suitable number and type of optical elements comprising an optical train such as that suggested in FIG. 1 as including iris 18, mirror 19 and lens 20. Luminescence from the probe molecules within sample 11 in the form of beam 21 is directed through a second optical train (such as lens 22, neutral density filter 23 and color filter 24 illustrated in the non-limiting system 10 embodiment) onto a second detector 25 (in the form of photomultiplier tube, photomultiplier, micro-channel plate, or photodiode). Signals 26,27 respectively from detectors 17,25 are directed into suitable electronic data storage means represented in FIG. 1 by digital storage oscilloscope 28. Signal 27 defines the luminescence output from probe 13 in sample 11. The purpose of beam portion 15R directed onto detector 17 is to provide an output signal 26 from detector 17 to initiate data acquisition from oscilloscope 28. It is noted, however, that data acquisition may be triggered directly by signal 27 from probe 13. Excess beam 15S energy passing through sample 11 may be absorbed by beam dump 29.

Figure 2A:
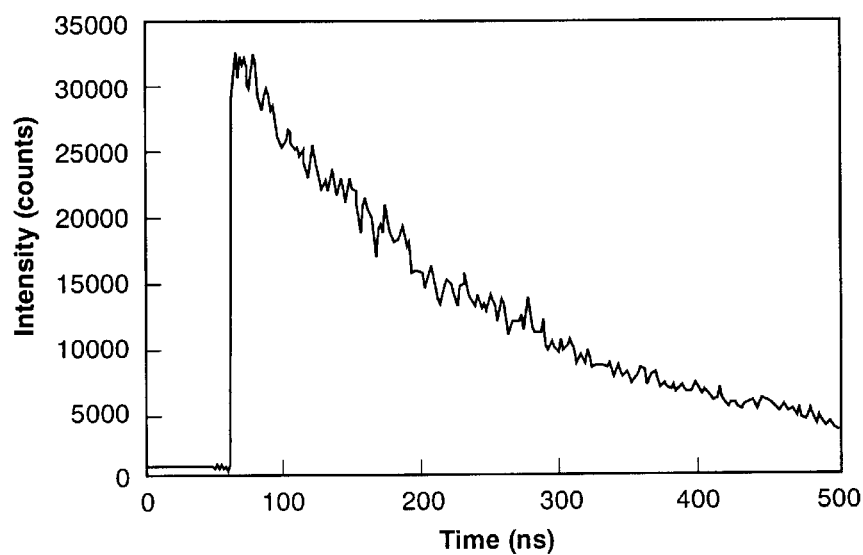
FIGS. 2a and 2b are plots of luminescence intensity of pyrene in cyclohexane and the natural logarithm of luminescence of pyrene in cyclohexane, respectively, versus time.
Figure 2B:
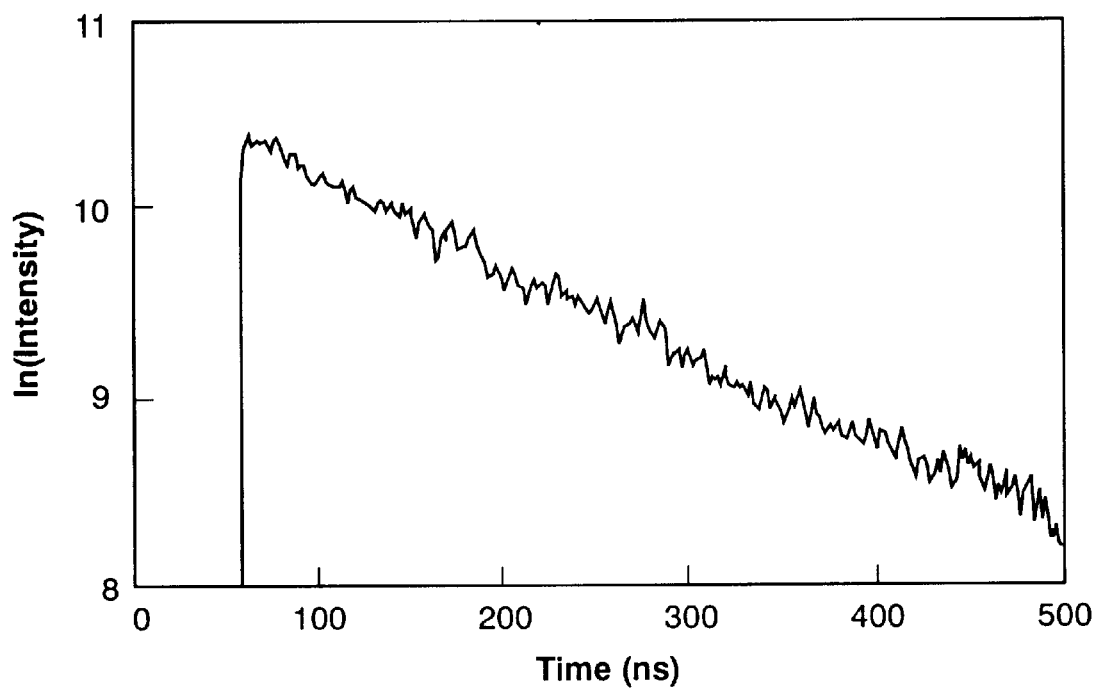

In demonstration of the method of the invention, cyclohexane and isooctane liquid fuels were tested for $O_2$ using pyrene as a luminophor probe. FIG. 2a shows decay of luminescence intensity of the excited pyrene as a function of time for a 9 ppm solution of pyrene in cyclohexane after sparging with nitrogen. FIG. 2b shows the data of FIG. 2a displayed as the natural logarithm of pyrene luminescence versus time. The lifetime of the luminescence may be obtained by directly fitting the exponential decays or by linearizing the data to determine lifetime using least squares. FIG. 2b shows the linearity of the logarithm of intensity decay over at least two orders of magnitude.

Figure 3:
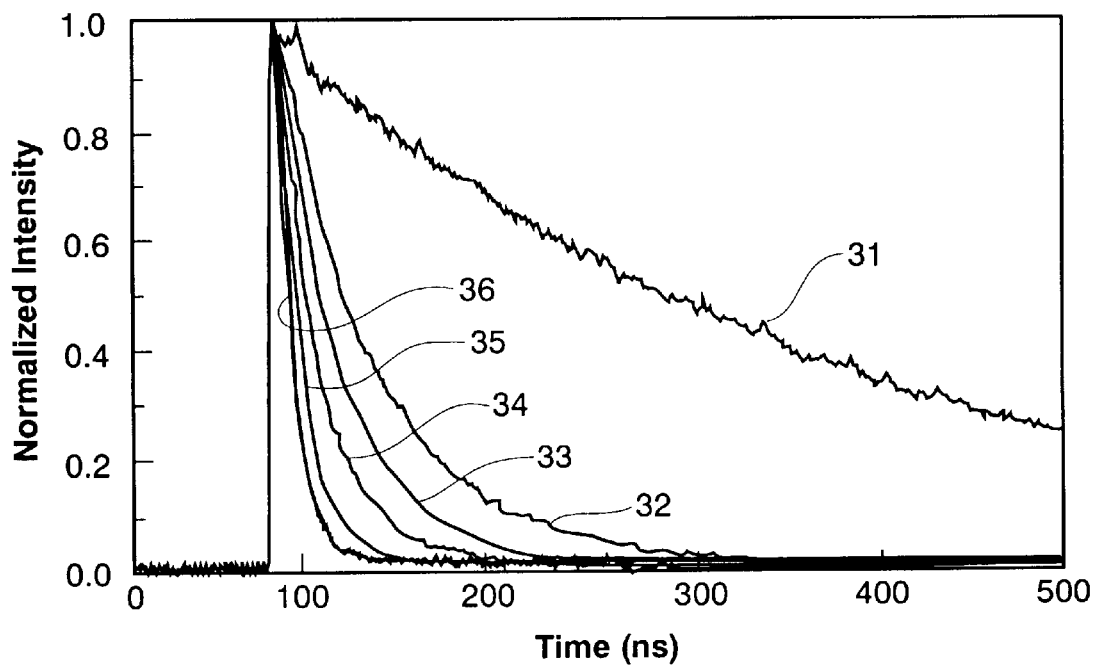
FIG. 3 is a plot of decay of pyrene luminophor probe luminescence intensity in isooctane versus time for varying oxygen concentrations.
Figure 4:
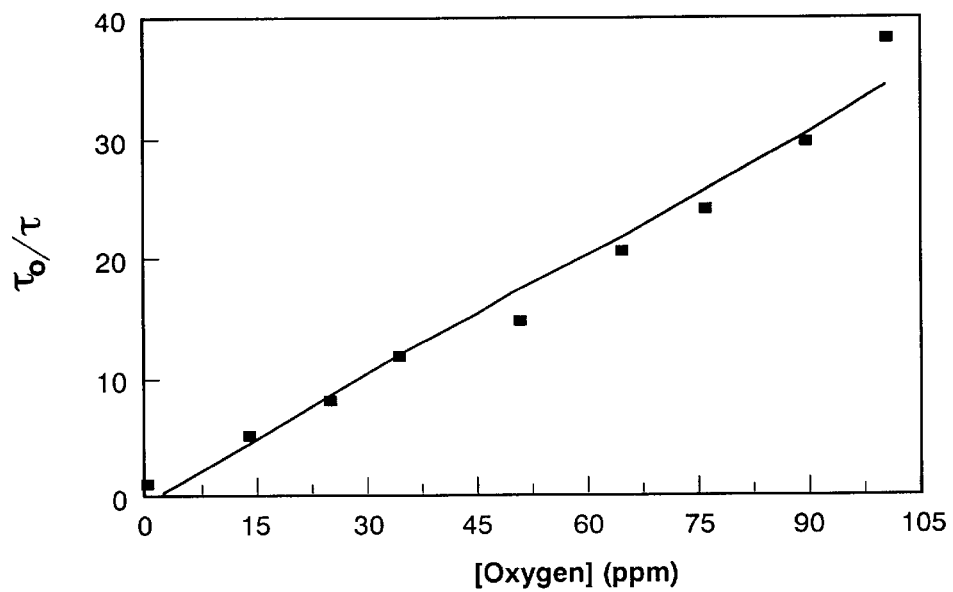
FIG. 4 is a calibration curve for oxygen concentration in isooctane using pyrene as a probe.

FIG. 3 is a plot of pyrene probe luminescence intensity decay in isooctane versus time for various oxygen concentrations illustrating the effect of luminescence quenching by oxygen. Curve 31 represents the longest luminescence lifetime for oxygen-free isooctane (0 ppm $O_2$ concentration). Curves 32,33,34,35,36 are luminescence decay traces of pyrene in isooctane, respectively, for $O_2$ concentrations of 16 ppm, 30 ppm, 40 ppm, 67 ppm and 101 ppm. Pyrene lifetime in isooctane clearly decreases with increased $O_2$ concentration in predictable fashion according to the principal teaching of the invention. FIG. 4 is a Stern-Volmer plot for $O_2$ quenching in the pyrene-isooctane system showing good linear dependence. FIG. 4 or the equivalent plot for other luminophor-liquid fuel systems may be used as a calibration curve for $O_2$ determination in the fuel.

Figure 5:
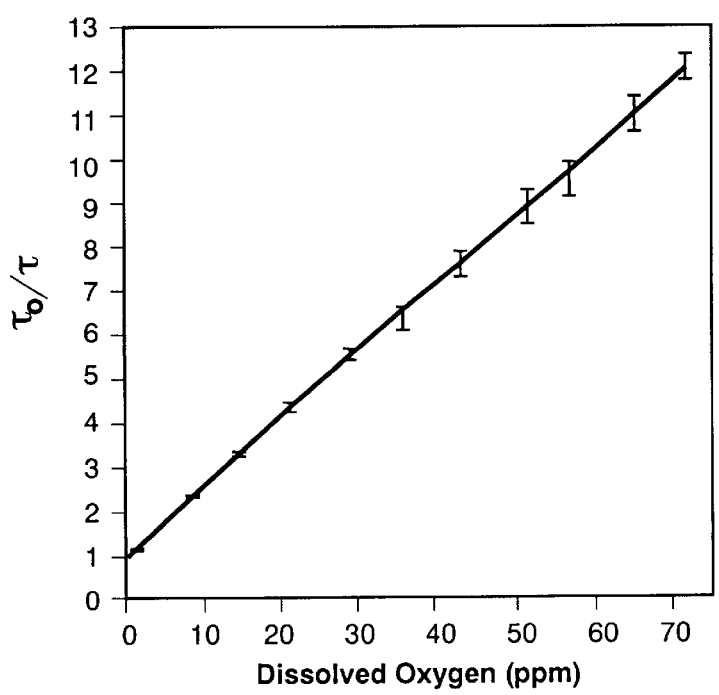
FIG. 5 is a calibration curve for oxygen concentration in jet-A fuel using pyrene as a probe.

The method of the invention was demonstrated on actual fuel samples in order to illustrate the best mode of operation of the invention. FIG. 5 shows a calibration curve for determination of $O_2$ concentration in Jet-A fuel at room temperature containing 10 ppm pyrene as the probe. The natural logarithm of the decay of luminescence intensity with time is linear. The lifetimes show a broad range from air saturated to fully unquenched giving good precision to the results. The pyrene could be decreased in concentration to the 1 ppm level without significantly diminishing the quality of results. All data were collected with a neutral density filter which reflects about 99% of the luminescence intensity.

The method of the invention was also demonstrated with flowing heptane fuel pumped through a heated tube simulating a jet fuel line. Pyrene at 0.1 to 100 ppm levels were added to the fuel in separate runs. The fuel reacts with the initially dissolved $O_2$, but system tightness prevents further absorption of $O_2$ into the fuel. By varying fuel flow rate through the tube the residence time of the fuel in the tube and hence the reaction time at high temperature may be varied. Oxygen concentration as a function of flow rate was measured to yield an $O_2$ consumption plot. Measurements using the method of the invention were compared against GC. The validity of the luminescence method of the invention was cross-checked by inserting an optical cell in-line with the GC. The fuel was returned to room temperature prior to the luminescence and GC measurements. It must be noted that the luminescence lifetime is temperature dependent, and control of temperature during comparative testing is therefore important.

Figure 6:
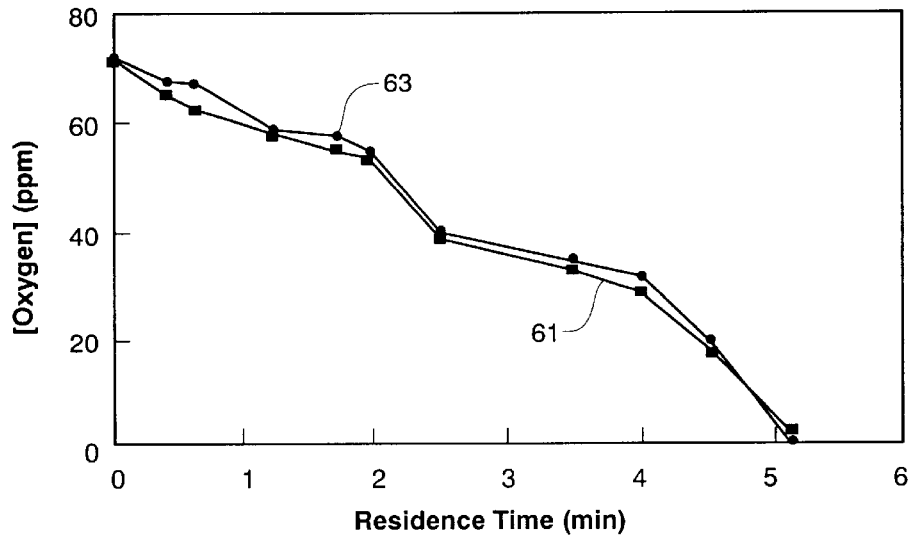
FIG. 6 is a plot of oxygen concentration versus residence time showing absolute oxygen concentration during aviation fuel thermal stress tests comparing the luminescence method of the invention to the GC method.
Figure 7:
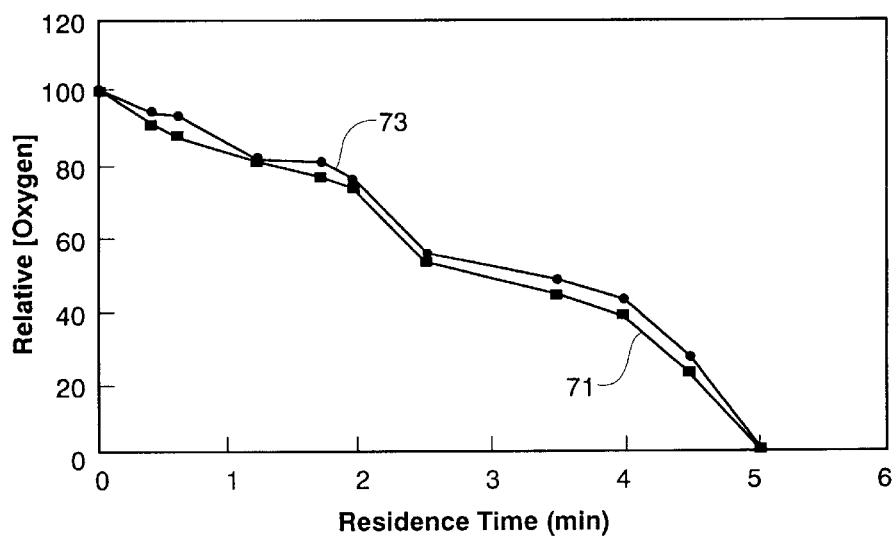
FIG. 7 is a plot of oxygen concentration versus residence time showing relative oxygen concentration during aviation fuel thermal stress tests comparing the luminescence method of the invention to the GC method.

FIG. 6 is a plot of $O_2$ concentration versus residence time showing absolute $O_2$ concentration during aviation fuel thermal stress tests comparing the method of the invention to GC. FIG. 7 is the corresponding plot of relative $O_2$ concentration versus residence time. In FIGS. 6 and 7, plots 61, 71 (defined by squares indicia) define measurements using the luminescence method of the invention and two-point calibration. Plots 63,73 (defined by circle indicia) define measurement results using GC. Accuracy and reproduceability of measurements using the method of the invention is apparent, including the structure of the decay curves, which reflects passivation effects characteristic of the heated simulated fuel line. Stem-Volmer plots of $\tau_0/\tau_q$ (see FIG. 5 supra) were used as calibration curves for data in FIG. 6. However, two point calibration can also be used. All generated Stern-Volmer plots were linear so that accurate measurement of the air-saturated and fully unquenched measurements were sufficient to define the calibration curves. Measurements of luminescence lifetime in the fuel at the slowest flow rate (at which all oxygen is consumed) and of the luminance lifetime of air-saturated fuel produces an accurate two-point calibration curve as illustrated in FIG. 7.

The luminescence lifetime may be obtained using a frequency-resolved rather than a time-resolved analysis as suggested in Gord et al, supra. The frequency-resolved method has lower cost and greater instrumental simplicity, but the time-resolved method gives better separation of background fuel luminescence from the probe luminescence.

The invention therefore provides a method for quantitatively determining dissolved oxygen in fuel. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A method for quantitating dissolved oxygen in liquid fuel, comprising the steps of:

(a) providing a sample of liquid fuel disposed within a sample region;

(b) doping said liquid fuel with a preselected concentration of a probe material comprising a luminophor which exhibits a luminescence which is quenched by oxygen dissolved in said liquid fuel;

(c) providing a source of light having a wavelength which induces said luminescence in said luminophor;

(d) illuminating said sample of liquid fuel with light from said source;

(e) measuring the change with time of said luminescence from said luminophor in said sample of liquid fuel; and (f) determining from said change with time of said luminescence the concentration of dissolved oxygen in said liquid fuel.

2. The method of claim 1 wherein said luminophor is a polycyclic aromatic hydrocarbon or a metal complex which when illuminated with light of a particular wavelength exhibits luminescence which is quenched by oxygen dissolved in said liquid fuel.

3. The method of claim 2 wherein said luminophor is selected from the group consisting of pyrene, anthracene and napthalene.

4. The method of claim 1 wherein said liquid fuel is selected from the group consisting of cyclohexane, isooctane, hexane, heptane, nonane, decane, kerosene and oil.

5. The method of claim 1 wherein said source is a coherent light source.

6. The method of claim 5 wherein said coherent light source is selected from the group consisting of a pulsed nitrogen laser, Eximer laser, Nd:YAG laser, Nd:YLF laser, Ti:sapphire laser, and Nd:YVO$_4$ laser.

* * * * *